United States Patent
Maroney et al.

(10) Patent No.: US 9,510,839 B2
(45) Date of Patent: *Dec. 6, 2016

(54) PROCEDURE FOR THE TREATMENT OF CUFF TEAR ARTHROPATHY

(75) Inventors: Brian J. Maroney, Fort Wayne, IN (US); Ian A. Trail, Greater Manchester (GB)

(73) Assignee: DePuy Synthes Products, Inc., Rayntham, MA (US)

( * ) Notice: Subject to any disclaimer, the term of this patent is extended or adjusted under 35 U.S.C. 154(b) by 802 days.

This patent is subject to a terminal disclaimer.

(21) Appl. No.: 13/361,114

(22) Filed: Jan. 30, 2012

(65) Prior Publication Data
US 2012/0130500 A1    May 24, 2012

Related U.S. Application Data

(63) Continuation of application No. 11/503,630, filed on Aug. 14, 2006, now Pat. No. 8,105,385, which is a
(Continued)

(51) Int. Cl.
*A61F 2/40*    (2006.01)
*A61B 17/15*    (2006.01)
(Continued)

(52) U.S. Cl.
CPC .............. *A61B 17/154* (2013.01); *A61F 2/40* (2013.01); *A61B 17/15* (2013.01); *A61B 17/164* (2013.01);
(Continued)

(58) Field of Classification Search
CPC ........................................................ A61F 2/40
(Continued)

(56) References Cited

U.S. PATENT DOCUMENTS 3,694,820 A    10/1972  Scales et al.
3,891,998 A    7/1975   Lennox
(Continued)

FOREIGN PATENT DOCUMENTS

DE    2041929 A1    3/1971
DE    2400650 A1    7/1974
(Continued)

OTHER PUBLICATIONS

Boileau et al., "Adaptability and Modularity in Shoulder Prostheses," Reprint from Maitrise Orthopedique, Sep. 1993, Tornier, France (10 pages).
(Continued)

*Primary Examiner* — Bruce E Snow
(74) *Attorney, Agent, or Firm* — Maginot, Moore & Beck, LLP

(57) ABSTRACT

A medical procedure for use in connection with a patient suffering from cuff tear arthropathy is disclosed. The medial procedure includes securing a prosthetic head component having a glenoid-bearing portion and an acromion-bearing portion to a humerus of a patient so that the glenoid-bearing portion is positioned in bearing contact with a glenoid surface of a scapula of the patient. The method further includes abducting the humerus so as to move the acromion-bearing portion of the prosthetic head component into direct contact with an acromion of the patient.

6 Claims, 10 Drawing Sheets

Related U.S. Application Data continuation of application No. 10/643,067, filed on Aug. 18, 2003, now abandoned, which is a continuation of application No. 09/767,473, filed on Jan. 23, 2001, now Pat. No. 6,620,197.

(51) Int. Cl.
 *A61B 17/16* (2006.01)
 *A61F 2/30* (2006.01)

(52) U.S. Cl.
 CPC .......... *A61B 17/1684* (2013.01); *A61F 2/4014* (2013.01); *A61F 2/4059* (2013.01); *A61F 2002/30332* (2013.01); *A61F 2002/30604* (2013.01); *A61F 2002/30612* (2013.01); *A61F 2002/30827* (2013.01); *A61F 2002/30884* (2013.01); *A61F 2002/30902* (2013.01); *A61F 2002/4018* (2013.01); *A61F 2002/4051* (2013.01); *A61F 2002/4062* (2013.01); *A61F 2002/4077* (2013.01); *A61F 2220/0033* (2013.01)

(58) Field of Classification Search
 USPC .......................................... 623/19.11–19.14
 See application file for complete search history.

(56) References Cited

U.S. PATENT DOCUMENTS

| | | |
|---|---|---|
| 3,978,528 A | 9/1976 | Crep |
| 3,979,778 A | 9/1976 | Stroot |
| 4,042,980 A | 8/1977 | Swanson et al. |
| 4,045,826 A | 9/1977 | Stroot |
| 4,257,128 A | 3/1981 | Scales et al. |
| 4,261,062 A | 4/1981 | Amstutz et al. |
| 4,279,041 A | 7/1981 | Buchholz |
| 4,355,427 A | 10/1982 | Schneider |
| 4,550,450 A | 11/1985 | Kinnett |
| 4,645,507 A | 2/1987 | Engelbrecht et al. |
| 4,662,888 A | 5/1987 | Field |
| 4,693,723 A | 9/1987 | Gabard |
| 4,759,350 A | 7/1988 | Dunn et al. |
| 4,865,605 A | 9/1989 | Dines et al. |
| 4,893,619 A | 1/1990 | Dale et al. |
| 4,919,669 A | 4/1990 | Lannelongue |
| 4,919,670 A | 4/1990 | Dale et al. |
| 5,041,117 A | 8/1991 | Engelhardt |
| 5,080,673 A | 1/1992 | Burkhead et al. |
| 5,234,432 A | 8/1993 | Brown |
| 5,282,865 A | 2/1994 | Dong |
| 5,314,479 A | 5/1994 | Rockwood, Jr. et al. |
| 5,330,531 A | 7/1994 | Capanna |
| 5,458,653 A | 10/1995 | Davidson |
| 5,489,309 A | 2/1996 | Lackey et al. |
| 5,489,310 A | 2/1996 | Mikhail |
| 5,540,695 A | 7/1996 | Levy |
| 5,549,682 A | 8/1996 | Roy |
| 5,658,340 A | 8/1997 | Muller et al. |
| 5,683,397 A | 11/1997 | Vendrely et al. |
| 5,702,457 A | 12/1997 | Walch et al. |
| 5,702,486 A | 12/1997 | Craig et al. |
| 5,720,752 A | 2/1998 | Elliott et al. |
| 5,728,161 A | 3/1998 | Camino et al. |
| 5,733,338 A | 3/1998 | Kampner |
| 5,776,194 A | 7/1998 | Mikol et al. |
| 5,782,920 A | 7/1998 | Colleran |
| 5,817,097 A | 10/1998 | Howard et al. |
| 5,876,459 A | 3/1999 | Powell |
| 5,885,297 A | 3/1999 | Matsen, III |
| 5,906,644 A | 5/1999 | Powell |
| 5,910,171 A | 6/1999 | Kummer et al. |
| 5,928,285 A | 7/1999 | Bigliani et al. |
| 5,944,757 A | 8/1999 | Grammont |
| 5,944,758 A | 8/1999 | Mansat et al. |
| 5,961,555 A | 10/1999 | Huebner |
| 5,980,526 A | 11/1999 | Johnson et al. |
| 5,997,543 A | 12/1999 | Truscott |
| 6,015,437 A | 1/2000 | Stossel |
| 6,045,582 A | 4/2000 | Prybyla |
| 6,171,341 B1 | 1/2001 | Boileau et al. |
| 6,283,999 B1 | 9/2001 | Rockwood, Jr. |
| 6,620,197 B2 * | 9/2003 | Maroney et al. ......... 623/19.14 |
| 8,105,385 B2 * | 1/2012 | Maroney et al. ......... 623/19.14 |

FOREIGN PATENT DOCUMENTS

| | | |
|---|---|---|
| DE | 3023354 A1 | 4/1981 |
| EP | 0460886 A1 | 12/1991 |
| EP | 0617934 A1 | 10/1994 |
| EP | 0845250 A2 | 6/1998 |
| FR | 2567019 A1 | 1/1986 |
| GB | 2297257 A | 7/1996 |
| GB | 2331016 A | 5/1999 |

OTHER PUBLICATIONS

Pearl et al., "Coronal Plane Geometry of the Proximal Humerus Relevant to Prosthetic Arthroplasty," Journal of Shoulder and Elbow Surgery, Jul./Aug. 1996, pp. 320-326, vol. 5, No. 4, Mosby-Year Book, Inc., St. Louis (9 pages).

Watson, "Bipolar Salvage Shoulder Arthroplasty," The Journal of Bone and Joint Surgery, 1996, pp. 124-127, vol. 78-B, No. 1, Tornier, Inc., Houston (4 pages).

\* cited by examiner

PROCEDURE FOR THE TREATMENT OF CUFF TEAR ARTHROPATHY

This application is a continuation of application Ser. No. 11/503,630, filed on Aug. 14, 2006 (now U.S. Pat. No. 8,105,385), which in turn is a continuation of application Ser. No. 10/643,067, filed on Aug. 18, 2003 (now abandoned), which in turn is a continuation of application Ser. No. 09/767,473, filed on Jan. 23, 2001 (now U.S. Pat. No. 6,620,197). The disclosure of the above-identified patents and patent application is hereby totally incorporated by reference in their entirety.

Cross reference is made to U.S. patent application Ser. No. 09/767,487 (now U.S. Pat. No. 6,780,190), entitled "Method and Apparatus for Resecting a Greater Tubercle from a Humerus of a Patient During Performance of a Shoulder Replacement Procedure" by Brian Maroney which is assigned to the same assignee as the present invention.

TECHNICAL FIELD OF THE INVENTION

The present invention relates generally to a procedure for the treatment of cuff tear arthropathy.

BACKGROUND OF THE INVENTION

During the lifetime of a patient, it may be necessary to perform a joint replacement procedure on the patient as a result of, for example, disease or trauma. One such type of joint replacement procedure is a shoulder replacement procedure in which a diseased and/or damaged shoulder joint is replaced with a prosthetic shoulder joint.

The need for a shoulder replacement procedure may be created by the presence of any one of a number of conditions. One such condition is the deterioration of the patient's rotator cuff. Specifically, an intact rotator cuff stabilizes the humeral head in the glenoid fossa of the scapula during abduction of the arm. While it is stabilized in such a manner, abduction of the arm causes the humeral head to translate only a short distance in the superior direction (e.g. a few millimeters) whereby a space is maintained between the humeral head and the acromion. However, for patients with rotator cuff arthropathy, significantly greater humeral excursion is observed. In particular, hyper-translation of the humeral head in the superior direction is observed in patients with massive rotator cuff deficiency thereby resulting in articulation between the superior surface of the humeral head and both the inferior surface of the acromion and the acromioclavicular joint during abduction of the patient's arm. Such articulation between these components accelerates humeral articular destruction and erosion of the acromion and acromioclavicular joint. Moreover, such bone-to-bone contact is extremely painful for the patient thereby significantly limiting the patient's range of motion. In short, patients with massive rotator cuff tear and associated glenohumeral arthritis, as is seen in cuff tear arthropathy, may experience severe shoulder pain, as well as, reduced function of the shoulder.

In order to treat patients suffering from cuff tear arthropathy, a number of prosthesis and techniques utilizing existing prosthesis have heretofore been designed. For example, surgeons have heretofore utilized a relatively large humeral head prosthesis in an attempt to completely "fill" the shoulder joint space. It was believed that such use of a large prosthesis would increase the efficiency of the deltoid muscle thereby improving motion of the shoulder. However, clinical experience has shown that such use of a large humeral head prosthesis "overstuffs" the shoulder joint thereby increasing soft tissue tension, reducing joint range of motion, and increasing shoulder pain. Moreover, such use of an oversized prosthetic head fails to resurface the area of the greater tubercle of the humerus thereby allowing for bone-to-bone contact between the greater tubercle and the acromion during abduction of the patient's arm.

A number of humeral head bipolar prostheses have also been utilized in an attempt to address the problems associated with cuff tear arthropathy. It was believed that the relatively unconstrained motion of the bipolar head would improve shoulder motion. However, heretofore designed bipolar prosthetic heads include relatively large offsets thereby overstuffing the shoulder joint in a similar manner to as described above. Moreover, scar tissue may form around the bipolar head thereby "freezing" the dual articulating motion of the prosthesis which has been known to create a large hemiarthroplasty that likewise overstuffs the shoulder joint. In addition, such bipolar prosthetic heads do not cover the articulating surface between the greater tubercle and the acromion thereby creating painful bone-to-bone contact therebetween.

Yet further, a number of techniques have heretofore been designed in which the relatively rough surface of the greater tubercle is smoothened with an osteotome or high-speed burr. Although this approach results in a smoother tubercle contact surface, relatively painful bone-to-bone articulating contact still occurs thereby reducing the patient's range of motion.

What is needed therefore is a method and apparatus for performing a shoulder replacement procedure for use in the treatment of cuff tear arthropathy which overcomes one or more of the above-mentioned drawbacks. What is particularly needed is a method and apparatus for performing a shoulder replacement procedure which eliminates painful articulation between the greater tubercle of the humerus and the acromion.

SUMMARY OF THE INVENTION

In accordance with one embodiment of the present invention, there is provided a method that includes securing a prosthetic head component having a glenoid-bearing portion and an acromion-bearing portion to a humerus of a patient so that the glenoid-bearing portion is positioned in bearing contact with a glenoid surface of a scapula of the patient. The method further includes abducting the humerus so as to move the acromion-bearing portion of the prosthetic head component into bearing contact with an acromion of the patient.

In accordance with another embodiment of the present invention, there is provided a medical procedure for use in connection with a patient suffering from cuff tear arthropathy. The method includes providing a humeral prosthesis having a prosthetic head component, wherein (i) the prosthetic head component includes a glenoid-bearing portion and an acromion-bearing portion, and (ii) the glenoid-bearing portion and the acromion-bearing portion define an outer bearing surface, and (iii) the outer bearing surface extends in a medial/lateral direction across a radial distance D, and (iii) D≥190°. The method further includes implanting the humeral prosthesis in the patient so that the acromion-bearing portion contacts and bears directly against a natural acromion of the patient during abduction of an arm of the patient that possesses the humerus.

In accordance with yet another embodiment of the present invention, there is provided a medical procedure that includes providing a humeral prosthesis having a prosthetic head component, wherein the prosthetic head component includes a glenoid-bearing portion and an acromion-bearing portion. The medical procedure further includes implanting the humeral prosthesis in the patient so that during abduction of an arm of the patient which possesses the humerus, (i) the acromion-bearing portion contacts and bears directly against a natural acromion of the patient, and (ii) the glenoid-bearing portion contacts and bears directly against at least a part of a natural glenoid surface of the patient.

DETAILED DESCRIPTION OF THE INVENTION

Figure 1:
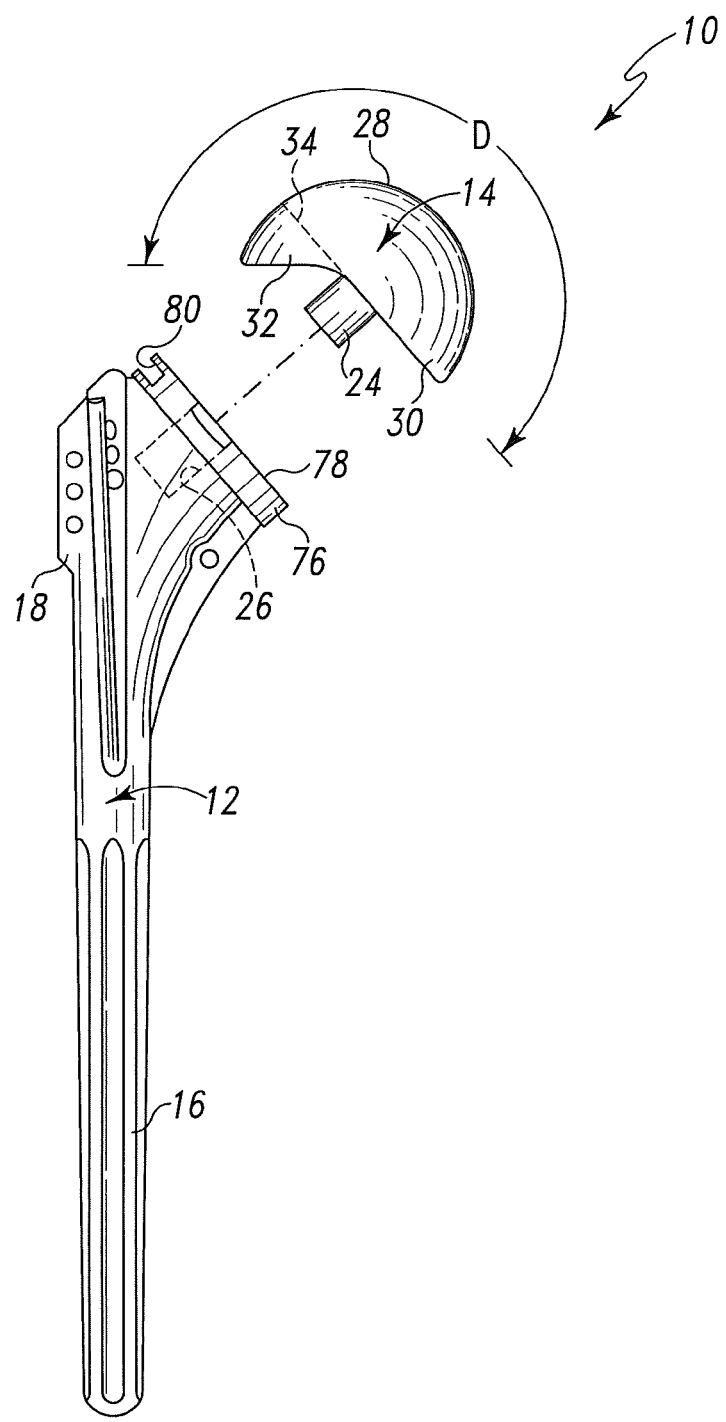
FIG. 1 is a perspective view of a humeral prosthesis which incorporates the features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 3:
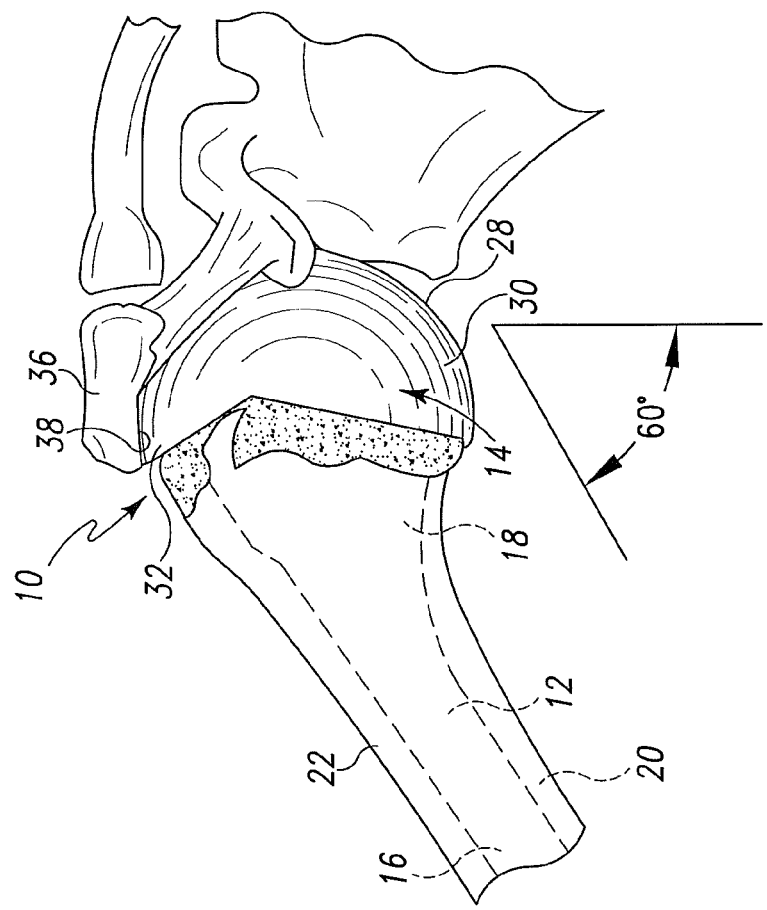
FIGS. 2 and 3 are diagrammatic views which show the humeral prosthesis of FIG. 1 implanted in the body of a patient.
Figure 2:
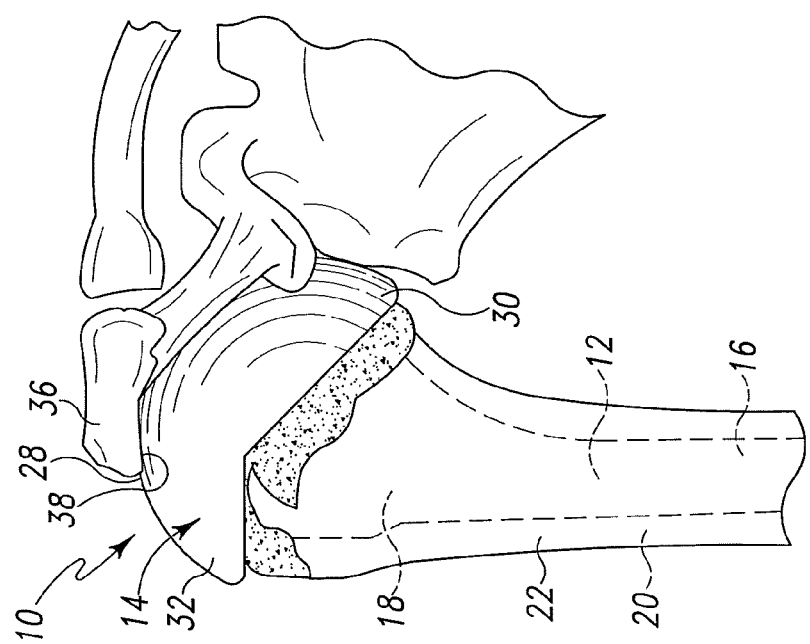

Referring now to FIGS. 1-3, there is shown a modular humeral prosthesis 10 which includes a stem component 12 and a head component 14. The stem component 12 includes an elongated stem portion 16 and a proximal body portion 18. It should be appreciated that, as used herein, the words proximal and distal are terms of reference that indicate a particular portion of a bone or prosthesis component according to the relative disposition of the natural bone or implanted prosthesis. Specifically, the term "proximal" indicates the portion of a component nearest the torso, whereas distal indicates the portion of a component farthest from the torso. Directional terms of reference which are used herein include superior, inferior, anterior, posterior, medial, and lateral. Such directional terms are used herein according to their commonly understood anatomical meanings. More specifically, with regard to a person positioned in a standing position, the term "superior" is utilized to mean upward, the term "inferior" means downward, the term "anterior" means forward, the term "posterior" means rearward, the term "medial" means inwardly from the side toward the center of the body, and the term "lateral" means outwardly from the center of the body toward the side.

Figure 14:
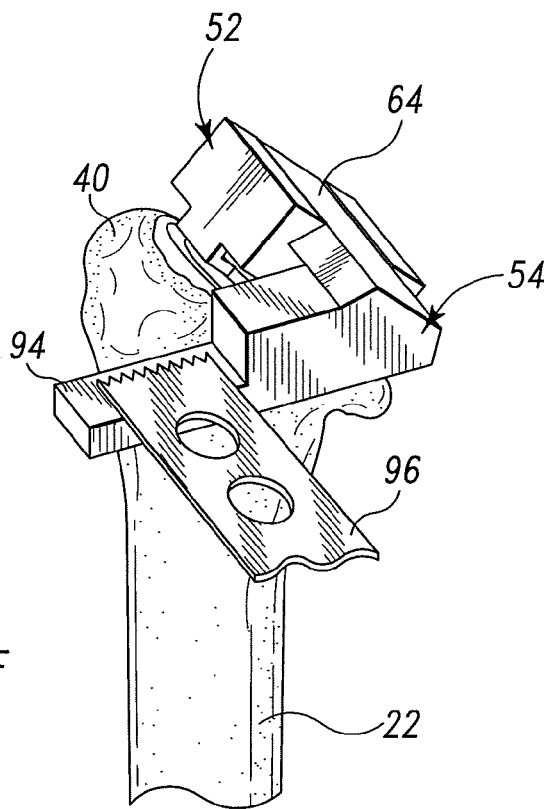
Figure 15:
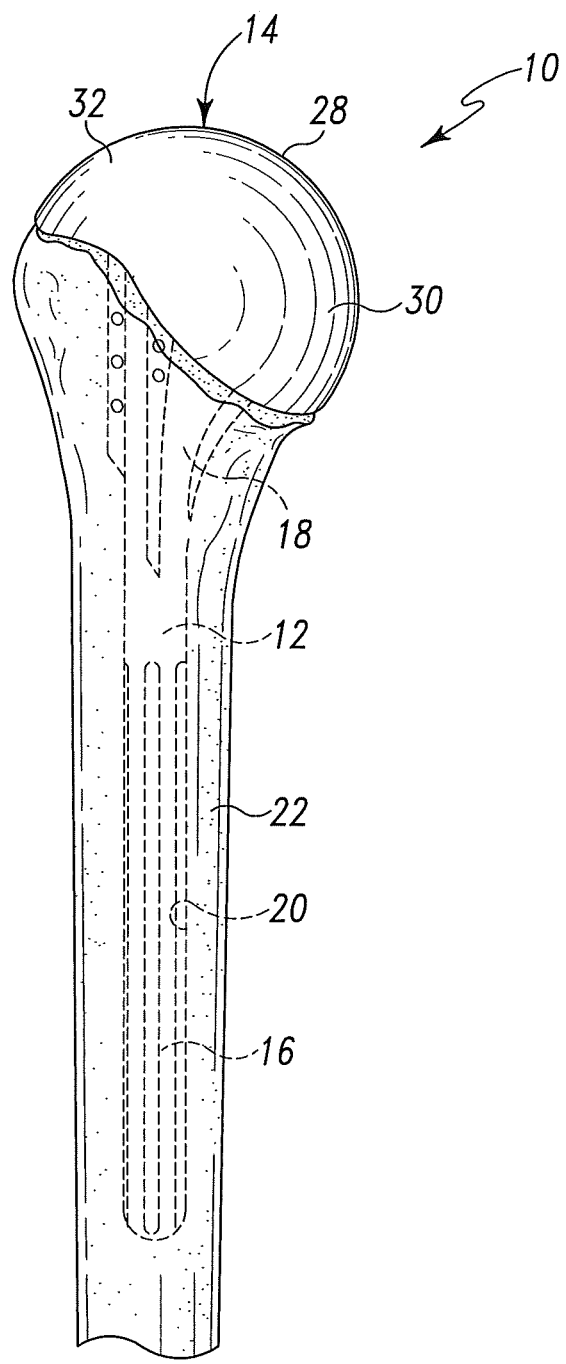

As shown in FIG. 14, the distal stem portion 16 of the stem component 12 is configured to be implanted into the medullary canal 20 of the patient's humerus 22 thereby securing the prosthesis 10 to the humerus 22. The proximal body portion 18 of the stem component 12 extends out of the proximal end of the humerus 22 in order for the head component 14 to be secured thereto. In particular, the head component 14 includes a tapered post 24 which is press fit or otherwise received into a corresponding tapered bore 26 defined in the proximal body portion 18 in order to secure the head component 14 to the stem component 12. Preferably, the head component 14 is secured to the stem component 12 prior to implantation of the stem component into the medullary canal 20 of the patient's humerus, although in situ securement of the head component 14 to the stem component 12 is also contemplated.

The head component 14 includes an outer bearing surface 28. The outer bearing surface 28 includes a glenoid-bearing portion 30 and an acromion-bearing portion 32. In particular, as shown in FIGS. 2 and 3, an imaginary line 34 divides the outer bearing surface 28 into (1) a first portion (i.e. the glenoid-bearing portion 30) which is essentially the same configuration as a standard, subhemispherically-shaped head component, and (2) a second portion (i.e. the acromion-bearing portion 32) which, in effect, extends the radial distance of the glenoid-bearing portion 30. Specifically, the outer bearing surface 28 extends a radial distance D in the medial/lateral direction (as viewed in FIGS. 2 and 3). The radial distance D across which the outer bearing surface 28 extends in the medial/lateral direction is greater than, or equal to, 190 degrees (i.e. D≥190°). In a more specific exemplary embodiment, the radial distance D across which the outer bearing surface 28 extends in the medial/lateral direction is approximately 220 degrees (i.e. D≈220°). However, it should be appreciated that the head component 14 may be configured to include an outer bearing surface 28 which extends across any desired radial distance between the range of, for example, 190 degrees and 270 degrees (i.e. 190°≤D≤270°).

Use of a prosthetic head component 14 having such a configuration (i.e. an outer bearing surface 28 possessing such an extended radial distance) is particularly advantageous during performance of a shoulder replacement procedure in the treatment of cuff tear arthropathy or any other ailment in which the patient's rotator cuff has been torn or otherwise separated from the humerus 22. In particular, as described above, in the absence of the rotator cuff, hyper-translation of the humeral head (or prosthetic head component) in the superior direction is observed. During abduction of the arm, such hyper-translation results in articulation between the humeral head (or prosthetic head component) and the patient's acromion 36 (along with the acromioclavicular joint). However, in the case of the prosthetic head component 14 of the present invention, the additional bearing surface area provided by the acromion-bearing portion 32 provides a low friction surface for articulating with an inferior surface 38 of the patient's acromion 36 thereby reducing, if not eliminating, pain associated with abduction of the patient's arm.

Figure 5:
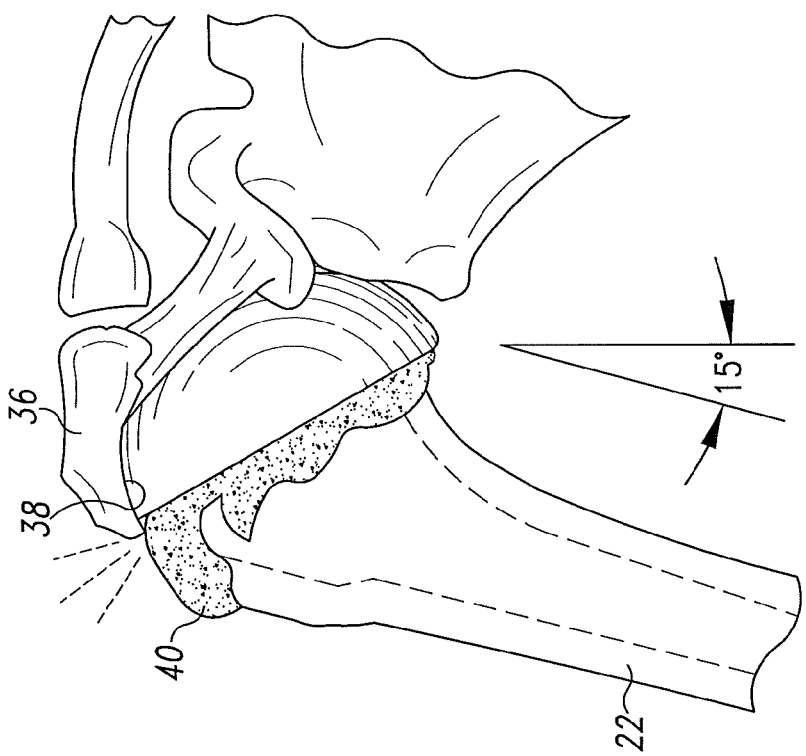
FIGS. 4 and 5 are views similar to FIGS. 2 and 3, but showing a humeral prosthesis having a standard, subhemispherically-shaped head component implanted in the body of the patient.
Figure 4:
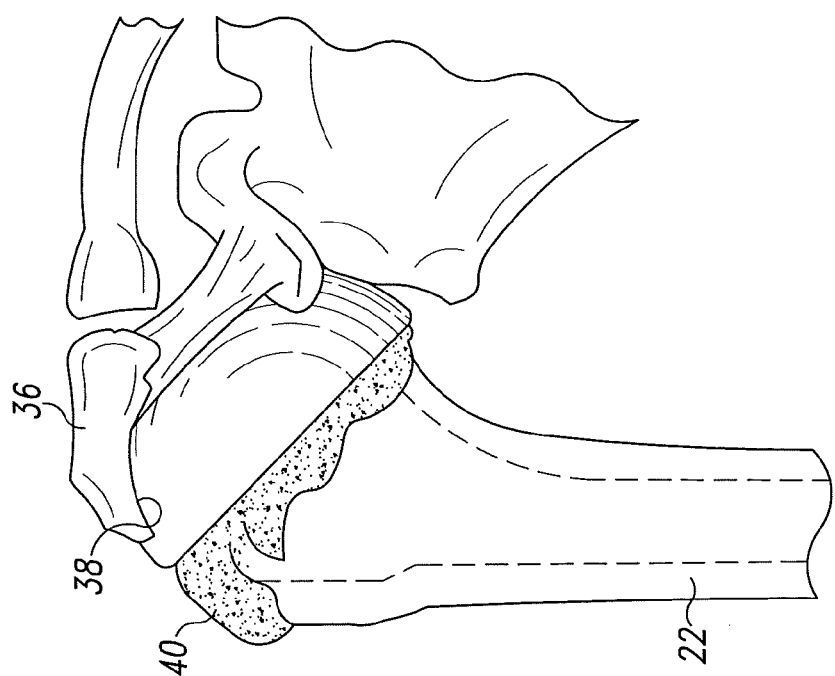

This is a significant improvement over heretofore designed prosthesis. For example, use of a standard, subhemispherically-shaped head component in regard to the treatment of cuff tear arthropathy is shown in FIGS. 4 and 5. As can been seen, the patient's acromion 36 articulates with the low friction outer surface of the subhemispherically-shaped head component through only approximately 15° of abduction of the patient's arm. Continued abduction of the patient's arm beyond such a range (i.e. 15°) results in painful bone-to-bone contact between the patient's acromion 36 and the patient's greater tubercle 40.

However, as can be seen in FIGS. 2 and 3, a significantly greater range of motion may be achieved by use of the prosthetic head component 14 of the present invention. In particular regard to the exemplary embodiment of the head component 14 described herein, the patient's acromion 36 articulates with the low friction outer surface bearing surface 28 of the head component 14 through over 60° of abduction of the patient's arm. This is due, in part, to the replacement of the patient's greater tubercle 40 with the acromion-bearing portion 32 of the prosthetic head 14. In particular, as will be discussed below in greater detail, during a surgical procedure according to the present invention, the natural head 98 of the patient's humerus 22 is first resected (see FIG. 7). Thereafter, the patient's greater tubercle 40 is then likewise resected (see FIG. 14). As a result, when the prosthesis 10 is implanted into the medullary canal 20 of the patient's humerus 22, the glenoid-bearing portion 30 of the head component 14 corresponds to the natural head 98 of the patient's humerus 22, whereas the acromion-bearing portion 32 corresponds to the greater tubercle 40 of the patient's humerus 22. What is meant herein by the term "correspond" when used in conjunction with a feature of the prosthesis 10 is that such a feature is located in approximately the same anatomic position as the natural anatomic feature that it replaced. Hence, the glenoid-bearing portion 30 of the head component 14 "corresponds" to the patient's natural humeral head 98 since it is located in approximately the same anatomical position as the natural head 98 subsequent to replacement thereof, whereas the acromion-bearing portion 32 of the head component 14 "corresponds" to the patient's greater tubercle 40 since it is located in approximately the same location as the greater tubercle 40 subsequent to replacement thereof.

It should be appreciated that resection of the greater tubercle 40 is preferably only performed when the patient is suffering from a massive rotator cuff tear. In particular, since the insertion points for certain of the muscles which form the rotator cuff are located on the greater tubercle 40, a surgeon would not typically resect the greater tubercle 40 unless the rotator cuff was already torn or otherwise rendered inoperative. This is true since, as described above, the rotator cuff, when functionally intact, stabilizes the humeral head in the glenoid fossa of the scapula during abduction of the arm thereby allowing the humeral head (or implanted prosthetic head component) to translate only a short distance in the superior direction (e.g. a few millimeters) during abduction of the patient's arm. Hence, when functionally intact, the rotator cuff prevents articulation (e.g. bearing contact) between the humeral head (or implanted prosthetic head component) and the patient's acromion 40. As a result, a surgeon would be clinically motivated to leave the greater tubercle 40 intact (including all muscle insertions associated therewith) in most, if not all, cases in which the rotator cuff is functionally intact.

As can therefore be appreciated from the above description, as used herein in regard to the greater tubercle 40, the terms "resect", "resecting", "resection", and "resected", when utilized to refer to the concepts of the present invention, are intended to mean any cutting or removal of a significant portion of the greater tubercle 40 including certain portions of the tubercle 40 utilized for muscle insertion. Hence, "resection" of the greater tubercle 40, as utilized herein, is intended to refer to the removal of greater portions of the greater tubercle 40 than would be removed in the case in which the surgeon desires to substantially retain the greater tubercle 40 in its preoperative condition and/or function such as in the case of when the surgeon desires to retain the functionality of the rotator cuff. For example, "resection" of the greater tubercle 40 may include the removal of bone associated with the greater tubercle to a point beyond the insertion point of the supraspinatus muscle. In any case, the term "resection" of the greater tubercle 40, as utilized herein, is intended to mean bone material removal to a degree beyond any slight shaving, smoothening, or "deburring" of the greater tubercle.

Figure 6:
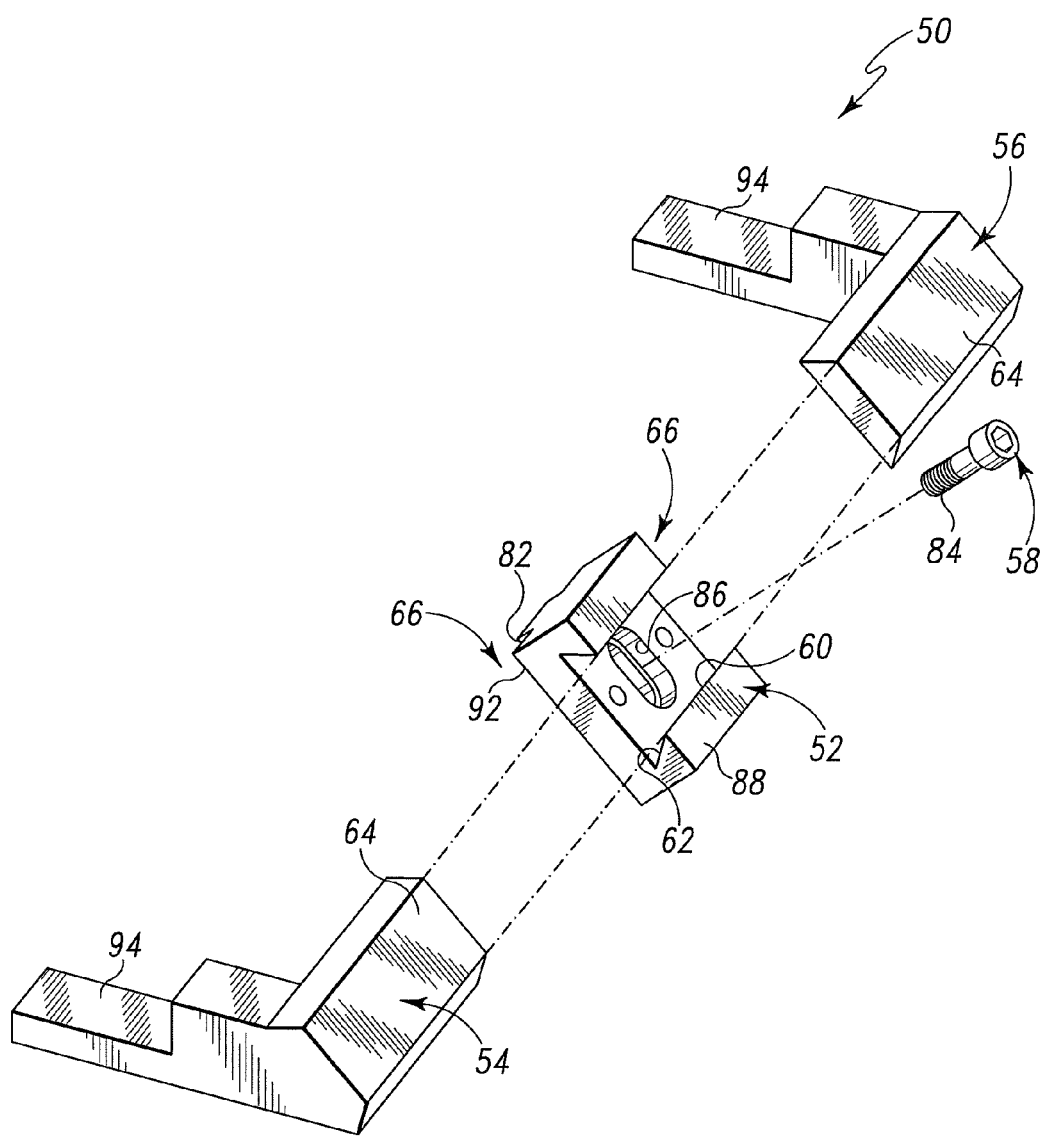
FIG. 6 is a perspective view of a surgical instrument assembly which incorporates the features of the present invention therein.

Referring now to FIG. 6, there is shown a surgical instrument assembly such as a cutting tool guide assembly 50 which is utilized during performance of a shoulder replacement procedure according to the present invention. The tool guide assembly 50 is particularly useful for guiding a cutting tool such as an oscillating bone saw or osteotome during cutting of the greater tubercle 40. For example, if during performance of a shoulder replacement procedure, a surgeon discovers that the patient's rotator cuff is torn or otherwise rendered inoperative due to, for instance, cuff tear arthropathy, the surgeon may utilize the tool guide assembly 50 during resection of the patient's greater tubercle 40 in order to allow for the use of the prosthetic head component 14.

The tool guide assembly 50 includes support block 52, a right guide member or block 54, a left guide member or block 56, and a fastener 58. The support block 52 includes a channel 60 which defines a mortise 62 for slidably receiving a projection or tenon 64 associated with the guide blocks 54, 56. In such a manner, the mortise 62 and the tenon 64 define a dovetail joint 66 which is utilized to selectively secure one of the guide blocks 54, 56 to the support block 52.

Figure 8:
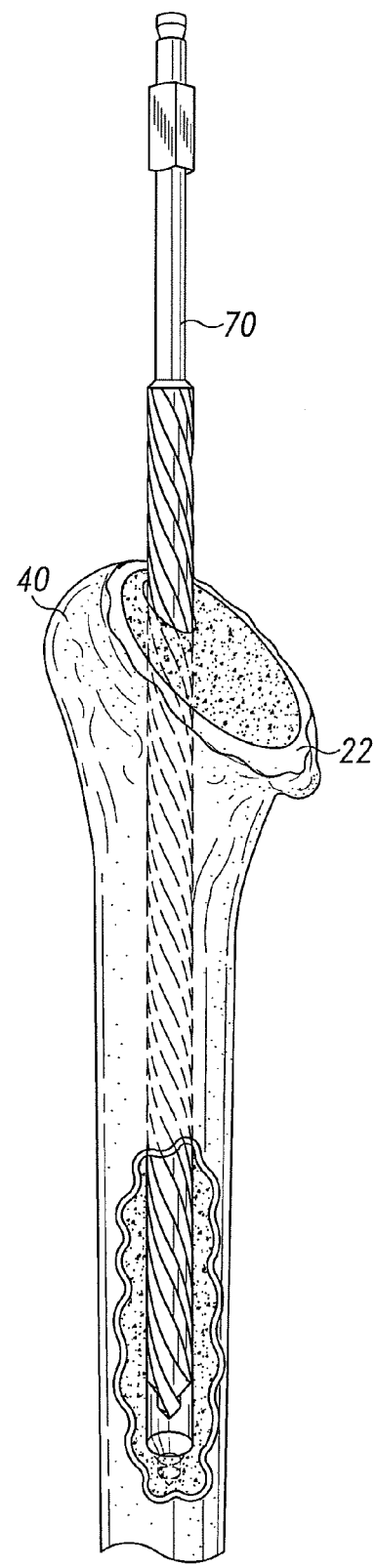
Figure 9:
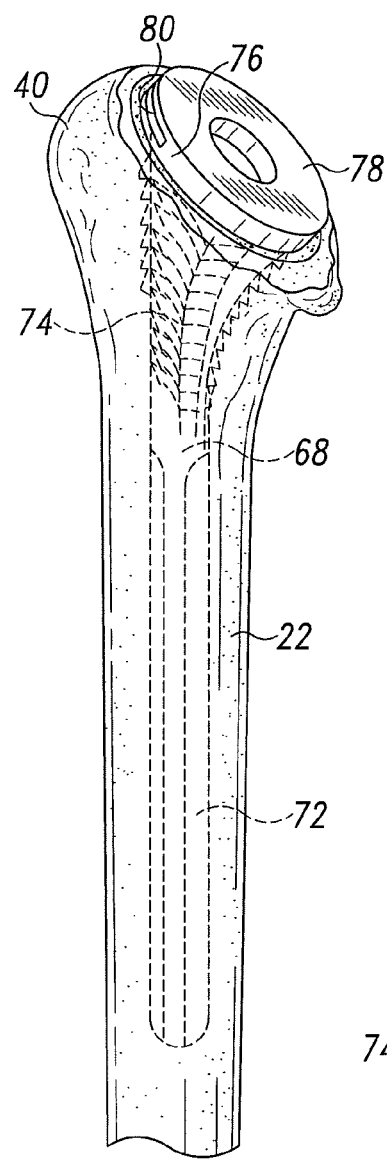
Figure 10:
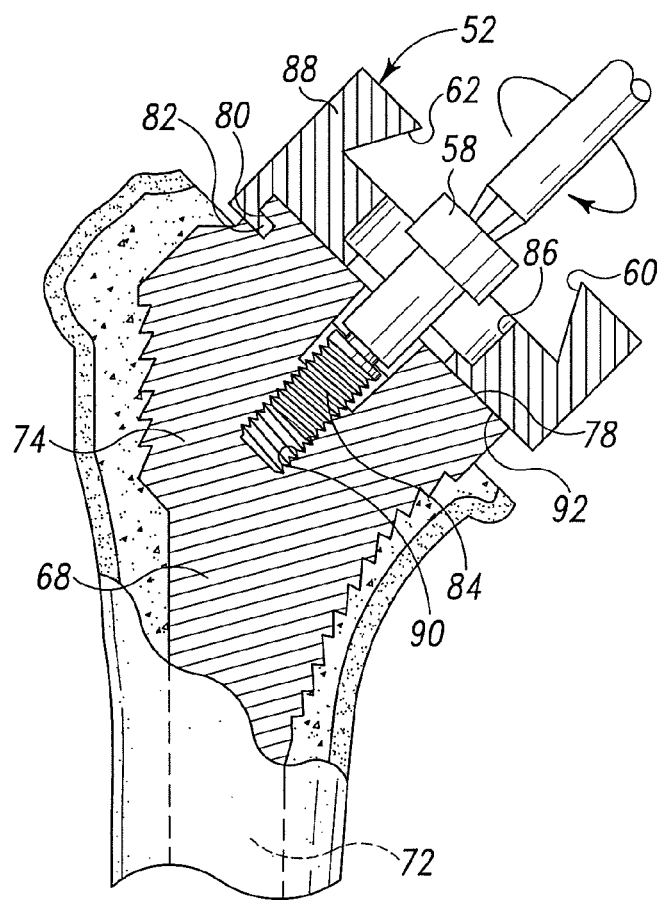
Figure 11:
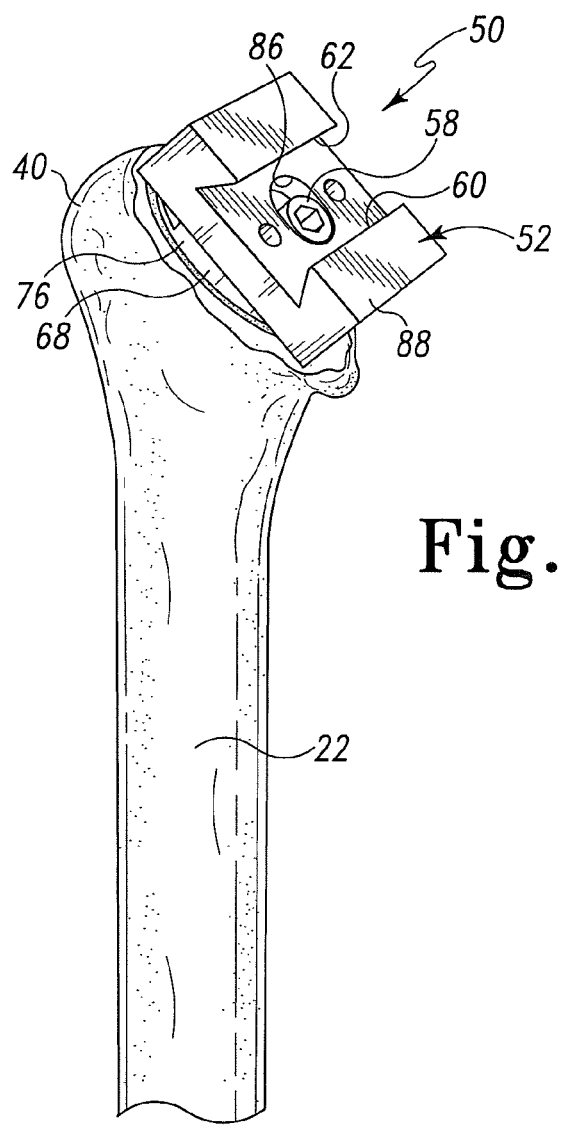

The guide blocks 54, 56 are securable to the humerus 22 of the patient in order to guide the surgeon during cutting of the greater tubercle 40. In particular, the support block 52 may first be secured to the humerus 22 by use of a positioning member. The positioning member may take any one of a number of different forms. For instance, in one exemplary embodiment, the positioning member may take the form of a surgical instrument such as an intramedullary broach 68 (see FIG. 9) or an intramedullary reamer 70 (see FIG. 8). In the case of the broach 68, as shown in FIGS. 9 and 10, the support block 52 is secured to a proximal end portion of the broach 68. Specifically, the broach 68 includes a distal end portion 72 which is advanced into the medullary canal 20 of the humerus 22 during a broaching operation. A proximal end portion 74 of the broach 68, on the other hand, extends out of the medullary canal 20, as shown in FIG. 9. The proximal end portion 74 of the broach 68 has a collar 76 having a face 78 and a slot 80 defined therein. A positioning tab 82 associated with the support block 52 is received into the slot 80 of the broach collar 76. Thereafter, the fastener 58 is utilized to secure the support block 52 to the broach 68. Specifically, a threaded end portion 84 of the fastener is advanced through a countersunk hole 86 defined in the base 88 of the support block 52 and into a counterbored hole 90 defined in the proximal end portion 74 of the broach 68. The threaded end portion 84 then threadingly engages a corresponding threaded portion of the counterbored hole 90 so as to advance and retain a bottom surface 92 of the base 88 of the support block 52 into firm contact with the face 78 of the collar 76 thereby securing the support block 52 to the broach 68 (see FIGS. 10 and 11).

It should be appreciated that, in lieu of the fastener 58, other configurations for securing the support block 52 to the broach 68 may also be utilized in accordance with the principles of the present invention. For example, in lieu of the fastener 58, a taper assembly such as a Morse taper assembly, a multi-sided post such as a hexagon-shaped post, or a clamping mechanism for clamping to the collar 76 may be utilized to secure the support block 52 to the broach 68.

Figure 13:
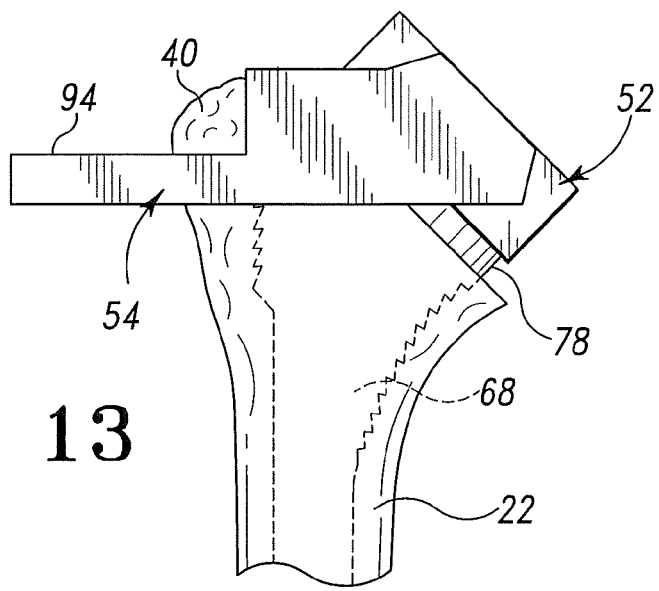

In any event, once the support block 52 is secured to the broach 68, the tenon 64 of either the right guide block 54 or the left guide block 56 (depending on whether the surgeon is operating on the patient's right or left humerus) is then slid into the mortise 62 of the support block 52. A pair of spring plungers (not shown) are utilized to retain the guide blocks 54, 56 in a desired location relative to the support block 52. As shown in FIG. 13, the configuration of the guide blocks 54, 56 and the support block 52 positions a tool guide surface 94 defined in the guide blocks 54, 56 in a predetermined location relative to the patient's humerus 22. In particular, the dimensions of the support block 52 and the guide blocks 54, 56 are predetermined so as to position the tool guide surface 94 in a location in which a surgeon may utilize the guide surface 94 to remove a predetermined portion of the patient's greater tubercle 40. For example, if a surgeon utilizes the guide surface 94 to guide a reciprocating bone saw 96 (see FIG. 14) or osteotome (not shown), a predetermined portion of the patient's greater tubercle 40 may be resected so as to allow for subsequent implantation of the prosthetic head component 14.

As shall be described below in regard to a shoulder replacement procedure according to the present invention, significant advantages are achieved by utilizing the implanted broach 68 as a positioning member for positioning the support block 52 (and hence the guide blocks 54, 56) in a desired position relative to the patient's humerus 22. However, certain of such advantages may be achieved by utilizing other types of positioning members for positioning the support block 52 (and hence the guide blocks 54, 56) in a desired position relative to the patient's humerus 22. For example, different types of surgical instruments may be utilized as positioning members for positioning the support block 52 (and hence the guide blocks 54, 56) in a desired position relative to the patient's humerus 22. For instance, as alluded to above, the support block 52 may be secured to a portion of the elongated shaft of an intramedullary reamer 70. Alternatively, the support block 52 may be secured to a trial implant stem (not shown) or to the implant stem (not shown) itself.

Moreover, either the support block 52, or the guide blocks 54, 56 themselves, may utilize a positioning member which allows the blocks 52, 54, 56 to be secured directly to the humerus 22 thereby eliminating the need to utilize a surgical instrument (e.g. the broach 68, reamer 70, trial implant stem, or implant stem) as a positioning member. In such a configuration, the support block 52 or the guide blocks 54, 56 may be configured to be utilized in conjunction with an attachment mechanism such as a pin assembly, clamping mechanism, or the like (not shown) for securing the same to the humerus 22 in a predetermined position relative to the humerus 22.

Yet further, the positioning member may also take the form of a fixture assembly or the like (not shown) which positions the support block 52 and/or the guide blocks 54, 56 in a predetermined position relative to the humerus 22 without actually being secured to the humerus 22. Specifically, such a fixture assembly may be secured to any one of the number of surgical components which are utilized during performance of a shoulder replacement procedure thereby eliminating the need to secure the support block 52 and/or the guide blocks 54, 56 to the humerus 22.

OPERATION OF THE PRESENT INVENTION

Figure 7:
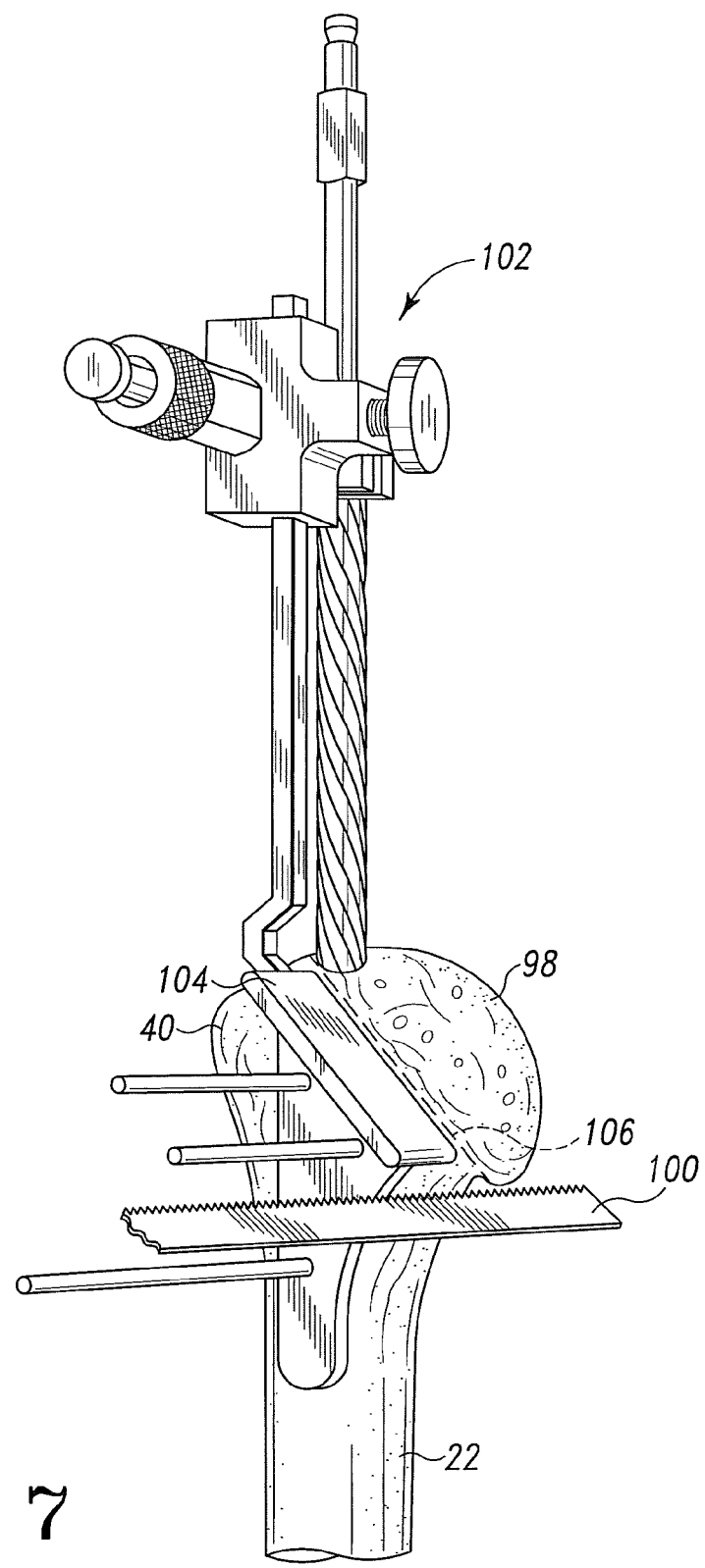
FIGS. 7-15 show a patient's shoulder during the various steps of a shoulder replacement procedure for the treatment of cuff tear arthroplasty according to the present invention.

In operation, the concepts of the present invention may be utilized to surgically treat a patient suffering from cuff tear arthropathy during performance of a shoulder replacement procedure. In order to do so, as shown in FIG. 7, the head 98 of the patient's humerus 20 is first resected by use of, for example, a bone saw 100. In particular, a head resection guide assembly 102 is first secured to the proximal end portion of the patient's humerus 22 in a conventional manner. A cutting guide 104 associated with the assembly 102 is then utilized to guide the blade of the bone saw 100 along a desired cutting path (shown as the dashed line 106) in order to resect a desired portion of the patient's natural head 98. It should be appreciated that the head resection procedure shown in FIG. 7 and described herein is quite similar to heretofore utilized head resection procedures which have been used during performance of shoulder replacement procedures in which the patient's rotator cuff is functionally intact (or believed to be functionally intact).

Once the natural head 98 of the patient's humerus 22 has been resected, the medullary canal 20 of the patient's humerus 22 is then surgically prepared. Specifically, as shown in FIG. 8, the reamer 70 is advanced into the medullary canal 20 of the patient's humerus 22 in order to ream the same. As with the head resection process described above in regard to FIG. 7, the reaming procedure shown in FIG. 8 and described herein is quite similar to heretofore utilized reaming procedures which have been used during performance of shoulder replacement procedures in which the patient's rotator cuff is functionally intact (or believed to be functionally intact).

Subsequent to reaming the medullary canal 20 of the humerus 22, a broaching procedure is performed in order to further prepare the medullary canal 20 for implantation of the stem component 12 of the prosthesis 10. Specifically, the distal end portion 72 of the broach 68 is advanced into the medullary canal 20 of the humerus 22 to a position in which the proximal end portion 74 of the broach 68 extends out of the medullary canal 20. As shown in FIG. 9, the broach 68 is advanced into the medullary canal 20 until fully seated in a position in which the collar 76 of the broach sits substantially flush with the resected surface of the humerus 22. Such broaching of the humerus 22, amongst other things, forms a cavity which is substantially equivalent in shape to the proximal body portion 74 of the stem component 68 (albeit slightly smaller to allow for press fitting of the stem component 68). Again, as with the head resection and reaming processes described above, the broaching procedure shown in FIG. 9 and described herein is quite similar to heretofore utilized broaching procedures which have been used during performance of shoulder replacement procedures in which the patient's rotator cuff is functionally intact (or believed to be functionally intact).

At this point, if the surgeon determines (or had previously determined) that the patient's rotator cuff is torn or otherwise no longer functionally intact, the surgeon may opt to prepare the patient's humerus 22 for implantation of a prosthesis that includes the prosthetic head component 14. In order to do so, the patient's greater tubercle 40 must first be resected. The steps associated with such resection of the patient's greater tubercle 40 are depicted in FIGS. 10-14. The first of such steps, as shown in FIG. 10, is the securement of the support block 52 to the broach 68. In particular, the positioning tab 82 associated with the support block 52 is first advanced into the slot 80 of the broach collar 76. Thereafter, the fastener 58 is utilized to secure the support block 52 to the broach 68. Specifically, the threaded end portion 84 of the fastener 58 is advanced through the countersunk hole 86 defined in the base 88 of the support block 52 and into threading engagement with the threaded portion of the counterbored hole 90.

Rotation (i.e. tightening) of the fastener 58 causes the bottom surface 92 of the base 88 of the support block 52 to be advanced into firm contact with the face 78 of the collar 76 thereby securing the support block 52 to the broach 68 (see FIG. 10).

Figure 12:
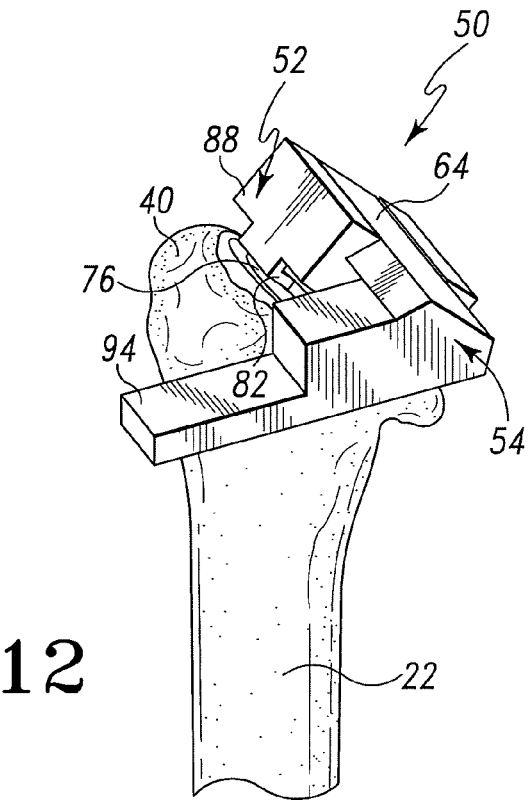

Once the support block 52 has been secured to the broach 68 in such a manner, the surgeon secures either the right guide block 54 or the left guide block 56 to the support block 52. Specifically, if the surgeon is performing the procedure on the patient's right shoulder, the surgeon selects the right guide block 54. Conversely, if the surgeon is performing the procedure on the patient's left shoulder, the surgeon selects the left guide block 56. In either case, as shown in FIG. 12, the tenon 64 of either the right guide block 54 or the left guide block 56 (again, depending on whether the surgeon is operating on the patient's right or left humerus) is slid into the mortise 62 of the support block 52. The block 54, 56 is advanced to a desired lateral position relative to the humerus 22 at which time a pair of spring plungers (not shown) are utilized to retain the guide blocks 54, 56 in a desired location relative to the support block 52.

As shown in FIG. 13, the configuration of the guide blocks 54, 56 and the support block 52 positions the tool guide surface 94 defined in the guide blocks 54, 56 in a predetermined location relative to the patient's humerus 22. In particular, the configuration of the support block 52 and the guide blocks 54, 56, when secured to the humerus 22 by use of the implanted broach 68, position the tool guide surface 94 in a location in which a surgeon may utilize the guide surface 94 to remove a predetermined portion of the patient's greater tubercle 40.

Indeed, once the required guide block 54, 56 has been secured to the support block 52 in the manner described above, a surgeon may utilize the guide surface 94 to guide a reciprocating bone saw 96 (see FIG. 14) or osteotome (not shown) in order to resect a predetermined portion of the patient's greater tubercle 40. Such resection is performed to provide for subsequent implantation of the prosthetic head component 14 during treatment of a patient suffering from cuff tear arthropathy.

Once the surgeon has completed the resection of the greater tubercle 40 by use of the bone saw 96, the surgeon disassembles the tool guide assembly 50 from broach 68. Specifically, the right guide block 54 or the left guide block 56 (depending on which one was utilized) is detached from the support block 52. Thereafter, the fastener 58 is unscrewed or otherwise removed from the broach 68 thereby allowing the support block 52 to be lifted away from the face 78 of the collar 76.

It should be appreciated that subsequent to removal of the tool guide assembly 50, a rasp or rongeur (not shown) may be utilized to extend the length of the cut created by the saw blade of the bone saw 96 in a medial direction to the point in which it intersects with the oblique cut created by the bone saw 100 during resection of the natural head 98 of the patient's humerus 22 (see FIG. 7). Moreover, the rasp or rongeur may also be utilized to remove any protruding bone sections which may subsequently interfere with proper seating of the prosthesis 10.

Once the surgeon has completed his or her use of the rasp or rongeur, the broach 68 is extracted from the medullary canal 22. Thereafter, the surgeon prepares the prosthesis 10 for implantation into the patient's humerus 22. Specifically, the surgeon selects both a stem component 12 and a head component 14 from a number of available sizes in order to select components which are properly sized for the patient's anatomy. It should be appreciated that the surgeon may employ any one of numerous techniques to determine the proper size of the stem component 12 and the head component 14 including the use of trial components which may be temporarily implanted into the humerus 22. For example, the surgeon may secure a trial head component to the broach 68 prior to extraction of the broach 68 in order to determine the proper size of the head component. It should also be appreciated that the surgeon generally selects a head component 14 which is sized quite similarly to the size of the patient's natural anatomy. This is a significant distinction from heretofore utilized methods in which the surgeon would generally select a head component which is larger in size than the natural head thereby "overstuffing" the shoulder joint as described above.

In any event, once the final combination of a properly sized stem component 12 and head component 14 has been selected, the two components are secured to one another. An impaction stand and associated impactor (not shown) may be utilized to engage the Morse taper associated with the two components. Specifically, the impaction stand and the impactor are utilized to advance and lock the tapered post 24 of the head component 14 into the corresponding tapered bore 26 defined in the proximal body portion 18 of the stem component 12 in order to secure the head component 14 to the stem component 12. Thereafter, as shown in FIG. 14, the prosthesis 10 is implanted into the medullary canal 20 of the patient's humerus 22.

Hence, as described herein, each of the prosthesis 10, the cutting tool guide assembly 50, and the associated surgical method of the present invention provides numerous advantages over heretofore designed prostheses, instrument assemblies, and surgical methods. For example, use of a prosthesis which includes the prosthetic head component 14 is particularly advantageous during performance of a shoulder replacement procedure in the treatment of cuff tear arthropathy or any other ailment in which the rotator cuff has been torn or otherwise irreparably separated from the humerus 22. In particular, as described above, in the absence of the rotator cuff, hyper-translation of the humeral head (or prosthetic head component) in the superior direction is observed. During abduction of the patient's arm, such hyper-translation results in articulation between the humeral head (or prosthetic head component) and the patient's acromion 36 (see FIGS. 2 and 3). However, in the case of the prosthetic head component 14 of the present invention, the additional bearing surface area provided by the acromion-bearing portion 32 provides a low friction surface for articulating with an inferior surface 38 of the patient's acromion 36 thereby reducing, if not eliminating, pain associated with abduction of the patient's arm.

Moreover, the prosthetic head component 14 may be utilized with existing stem component designs. This is particularly useful since it eliminates the need to design a dedicated stem component for use only with the head component 14. As a result, a hospital or medical facility may reduce the number of different types of stem components which must be maintained in its inventory since the same stem component may be utilized for either a standard, subhemispherically-shaped prosthetic head component or the head component 14 of the present invention.

Yet further, the cutting tool guide assembly 50 of the present invention provides for relative ease in the resection of the greater tubercle 40. Specifically, the tool guide assembly 50 provides a surgical instrument assembly which may be utilized by the surgeon to easily and accurately determine the proper cutting plane for resecting the greater tubercle 40.

Such an assembly does not exist in heretofore designed surgical instrument assemblies.

Moreover, the cutting tool guide assembly 50 of the present invention provides for relatively efficient resection of the greater tubercle 40 since, in certain exemplary embodiments, it is designed to be secured to the broach 68. Indeed, by configuring the cutting tool guide assembly 50 to be secured to the broach 68, additional time consuming surgical steps are avoided. Specifically, by securing the cutting tool guide assembly 50 to the broach 68, use of additional support members such as additional surgical instruments is avoided.

Yet further, the surgical method of the present invention provides flexibility in regard to the type of procedure which may be performed by the surgeon. In particular, since the initial steps of the surgical procedure of the present invention (e.g. the steps up to and including broaching of the medullary canal 20 of the humerus 22) are substantially the same as those steps which would be performed in the case of when the rotator cuff is intact, the surgeon may make the decision to resect the greater tubercle 40 (and thereafter utilize the prosthetic head component 14) in situ. For example, if the surgeon begins a shoulder replacement procedure under the belief that the rotator cuff is somewhat intact only to find out during the procedure that the rotator cuff is, in fact, functionally inoperative, the surgeon may "convert" the procedure into a procedure which also "replaces" the greater tubercle 40 by simply attaching the cutting guide assembly 50 to the broach 68 (which would be present anyway) and thereafter completing the procedure (including the use of the prosthetic head 14 as opposed to a standard, subhemispherically-shaped head) in the manner described above. Hence, the surgical procedure of the present invention is particularly useful in clinical situations in which the surgeon cannot accurately determine preoperatively the condition of the patient's rotator cuff.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the prosthesis, surgical instrument assembly, and associated methods described herein. It will be noted that alternative embodiments of each of the prosthesis, surgical instrument assembly, and associated methods of the present invention may not include all of the features described yet still benefit from at least some of the advantages of such features. Those of ordinary skill in the art may readily devise their own implementations of a prosthesis, surgical instrument assembly, and/or associated methods that incorporate one or more of the features of the present invention and fall within the spirit and scope of the present invention as defined by the appended claims.

What is claimed is:

1. A method, comprising:
   securing a prosthetic head component having a glenoid-bearing portion and an acromion-bearing portion to a humerus of a patient so that said glenoid-bearing portion is positioned in bearing contact with a glenoid surface of a scapula of said patient; and
   abducting said humerus so as to move said acromion-bearing portion of said prosthetic head component into direct contact with an acromion of said patient.

2. The method of claim 1, further comprising resecting a head of said humerus of said patient prior to said securing step.

3. The method of claim 2, further comprising resecting a greater tubercle of said humerus of said patient prior to said securing step.

4. The method of claim 1, wherein said securing step includes the step of positioning said glenoid-bearing portion of said prosthetic head component in direct contact with a natural glenoid surface of said scapula.

5. The method of claim 1, wherein said positioning step includes the step of positioning said glenoid-bearing portion of said prosthetic head component in direct contact with a prosthetic glenoid surface secured to said scapula.

6. The method of claim 1, wherein said abducting step includes the step of abducting said humerus so as to move said acromion-bearing portion of said prosthetic head component into direct contact with an inferior surface of said acromion of said patient.

* * * * *